(12) United States Patent  
Ooshima et al.

(10) Patent No.: US 6,674,462 B1
(45) Date of Patent: Jan. 6, 2004

(54) VIDEOSCOPE AND ITS DISPLAY UNIT (75) Inventors: Kiyoko Ooshima, Shijonawate (JP); Hiroshi Atsuta, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/528,623

(22) Filed: Mar. 20, 2000

(30) Foreign Application Priority Data

Mar. 19, 1999 (JP) ............................................ 11-075289

(51) Int. Cl.[7] .......................... H04N 15/00; A61B 1/04; G02B 27/22
(52) U.S. Cl. .......................... 348/42; 600/111; 359/462
(58) Field of Search ............................ 348/45, 51, 335, 348/344, 42; 600/111, 166; 359/462, 464, 465, 618, 636, 639; 396/327, 33, 330

(56) References Cited

U.S. PATENT DOCUMENTS 4,674,853 A * 6/1987 Street ........................ 396/330
5,860,912 A * 1/1999 Chiba ........................ 600/111
5,907,434 A * 5/1999 Sekine et al. ................ 359/462
6,547,720 B1 * 4/2003 Street ........................ 600/111

FOREIGN PATENT DOCUMENTS

| EP | 0575257 A2 * | 6/1993 | .......... G02B/27/00 |
| EP | 0 575 257 A2 A3 | 6/1993 | |
| JP | HEI 8-29701 | 2/1926 | |
| JP | 8-265804 | 10/1996 | |

OTHER PUBLICATIONS

International Search Report corresponding to application No. EP 00 10 5551 dated Apr. 16, 2002.

* cited by examiner

Primary Examiner—Gims Philippe
(74) Attorney, Agent, or Firm—RatnerPrestia (57) ABSTRACT Light is divided into transmitted light and reflected light by a half mirror 3. The transmitted light is photographed by a first imaging system and the reflected light is photographed by a second imaging system. In this case, a very-small binocular parallax is realized by parallax producing means 7S and 7K.

9 Claims, 8 Drawing Sheets

VIDEOSCOPE AND ITS DISPLAY UNIT

BACKGROUND OF THE INVENTION

1. Field of the Invention

The present invention relates to a videoscope for three-dimensionally viewing a skin, a tissue sample or the like by enlarging it through close-up photography, and its display unit.

2. Description of the Related Art

Though a scope using a solid-state imaging sensing device such as a CCD (hereafter referred to as CCD) is recently used for observation of a skin, it is difficult to identify the irregularity of a skin groove, a skin crest, or lesion. Therefore, a scope allowing three-dimensional observation is requested.

That photographing methods for three-dimensional reproduction include a parallel imaging method of arranging two cameras so that optical axes are parallel and an intersectional imaging method in which optical axes intersect each other is announced through various books and theses including "Foundation of Three-Dimensional Image" edited by NHK Science & Technical Research Laboratories and it is publicly known that an image photographed by the parallel imaging method or intersectional imaging method is deformed and reproduced except a state under a certain condition.

Moreover, three-dimensional display units for reproducing a three-dimensional image include the polarization-filter type using special glasses such as polarization glasses, liquid-crystal shutter type for time-division display of right and left images, and parallax barrier type requiring no glasses, and lenticular type.

As a scope for three-dimensional observation, Japanese Patent Laid-Open No. Hei8-29701 discloses a three-dimensional endoscope having two imaging windows constituted by arranging imaging systems comprising a pair of object lenses and a CCD in parallel or collaterally so as to obtain a binocular parallax and a display unit for displaying right and left images through time division and observing the images by special glasses.

In case of three-dimensional viewing, there is a binocular fusion limit in which binocular fusion is not realized when a binocular parallax increases to a certain degree or higher.

Moreover, when a distance from an object is too small like the case of close-up enlargement, a fusion range of right and left reproduced images is too small in case of the parallel imaging method when a binocular parallax is too large while a degree of trapezoidal deformation of a reproduced image further increases in case of the intersectional imaging method. Thus, it is difficult to obtain a preferable three-dimensional image. Therefore, it is necessary to realize a small binocular parallax.

Figure 7:
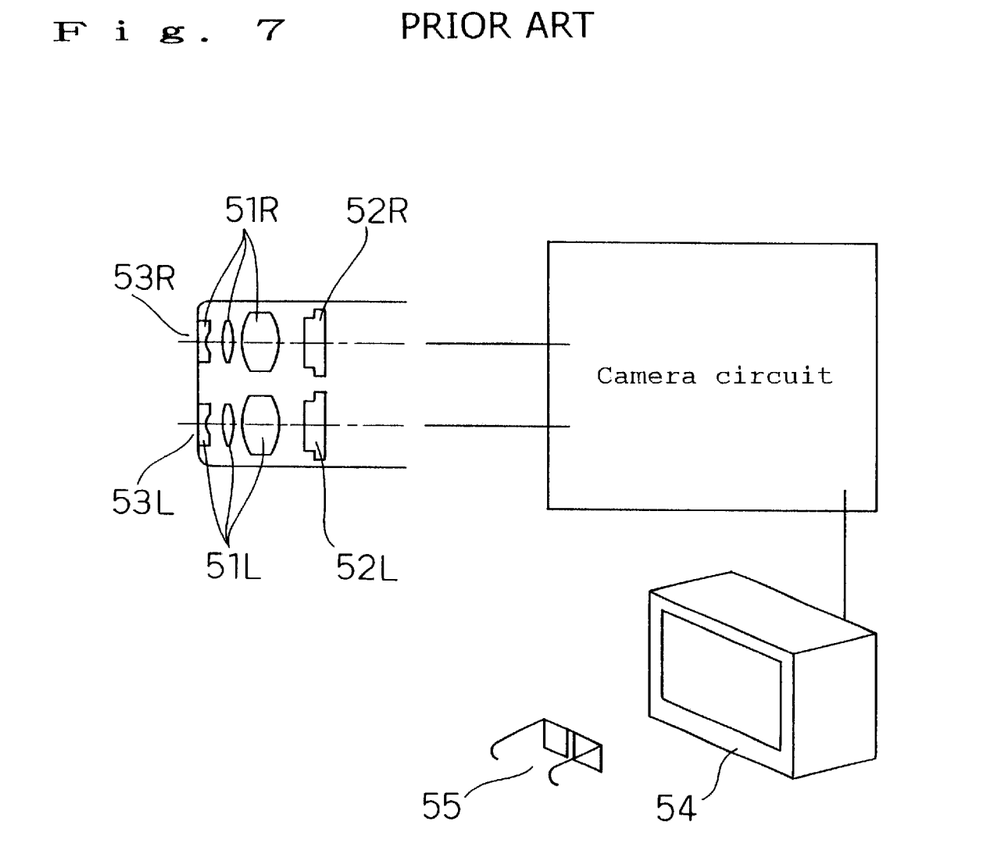
FIG. 7 is an illustration of a three-dimensional viewing system of a conventional example.

However, as shown in FIG. 7, the prior art disclosed in Japanese Patent Laid-Open No. Hei8-29701 fixes two imaging systems comprising objective lenses 51R and 51L and CCDs 52R and 52L in parallel or collaterally and images an object from two imaging windows 53R and 53L.

In case of the above configuration, the interval between objective lenses for forming a convergence angle is restricted to the size of an objective lens and it is impossible to realize a very-small binocular parallax necessary for close-up enlargement photography.

Moreover, a display unit 54 of the prior art is inferior in manipulability because it is troublesome to set or remove special glasses 55, a screen image is dark because of using a polarization filter, vertical resolution deteriorates to ½, or a flicker occurs or a double-speed-display converter for preventing the flicker is necessary.

SUMMARY OF THE INVENTION

The present invention is made to solve the problems of a conventional three-dimensional videoscope and its object is to provide a display unit capable of obtaining a preferable three-dimensional image through close-up photography and a simple display unit superior in manipulability.

One aspect of the present invention is a videoscope, comprising:
  light dividing means for dividing the light incoming from an imaging window and emitted from an object into transmitted light and reflected light;
  a first imaging system having at least an objective lens and an imaging device for imaging the transmitted light; and
  a second imaging system having at least an objective lens and an imaging device for imaging the reflected light, wherein:
    image inverting means for returning a mirror image formed by the reflected light to an orthoscopic image is provided for the second imaging system; and
    parallax producing means for producing a parallax for three-dimensionally viewing an image formed by the first and second imaging systems is included.

Another aspect of the present invention is a display unit, characterized by comprising image synthesizing means for producing images for one frame by deleting predetermined areas of a first video signal and a second video signal which are provided with a parallax for three-dimensional viewing so as to leave central portions and arranging video signals of central portions to right and left and outputting the images for one frame as video signals.

BRIEF DESCRIPTION OF THE DRAWINGS

FIGS. 6(*a*) and 6(*b*) are illustrations of video-signal contracting directions of the present invention.

DESCRIPTION OF SYMBOLS

1 Videoscope
2 Imaging window
3 Half mirror
4S, 4K Objective lens
5S, 5K CCD
7S, 7K Inching-mechanism portion
8S, 8K Camera circuit 8D Synchronous circuit
V1 First video-signal output
V2 Second video-signal output
11, 31 Display unit
12R First monitor screen
12L Second monitor screen
13, 34 Field-of-view limiting portion
35 Image synthesizing circuit

DESCRIPTION OF THE PREFERRED EMBODIMENTS

Embodiments of the present invention are described below by referring to FIGS. 1 to 5.

(Embodiment 1)

Figure 1:
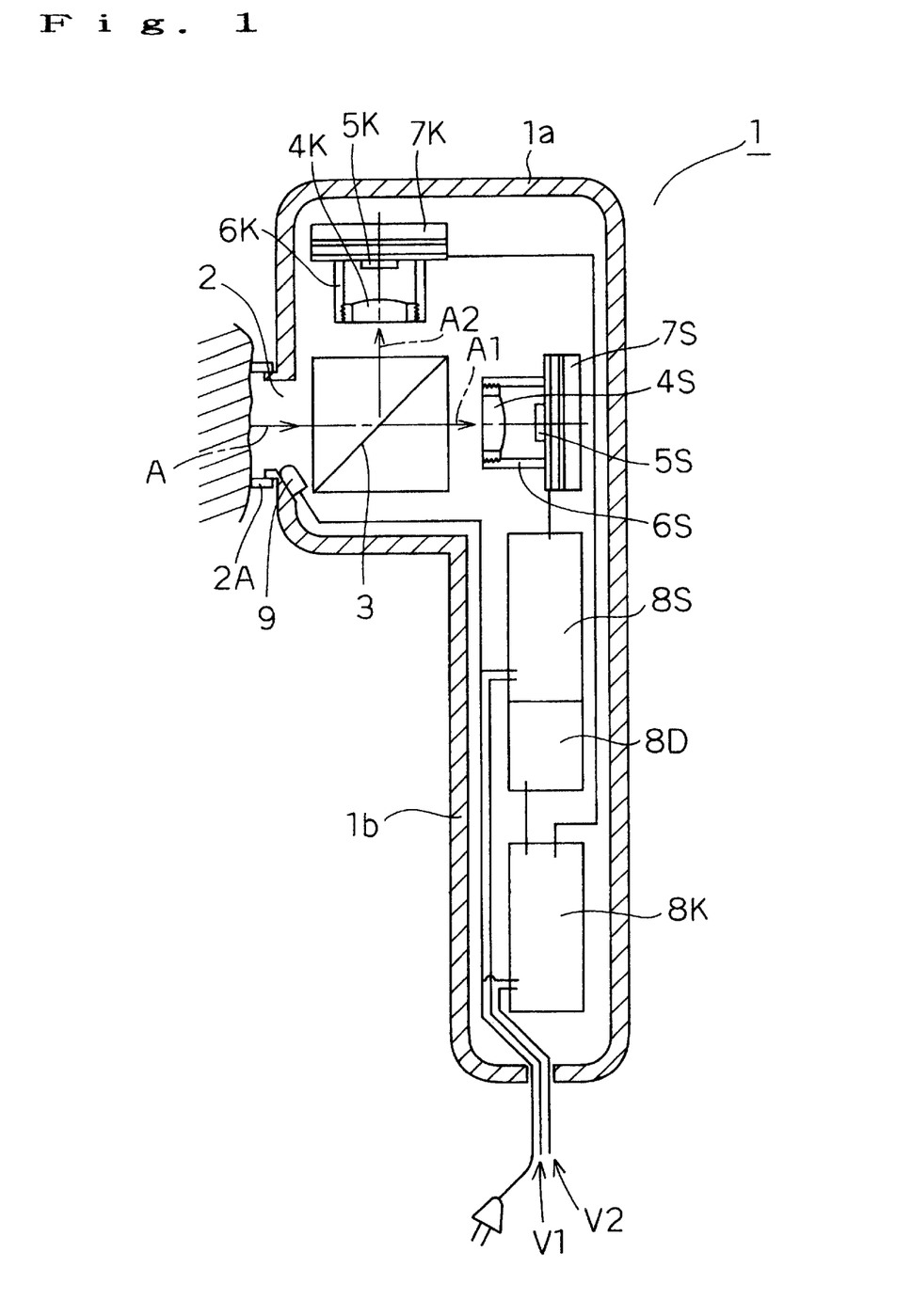
FIG. 1 is a schematic block diagram of a videoscope of embodiment 1 of the present invention.
Figure 2:
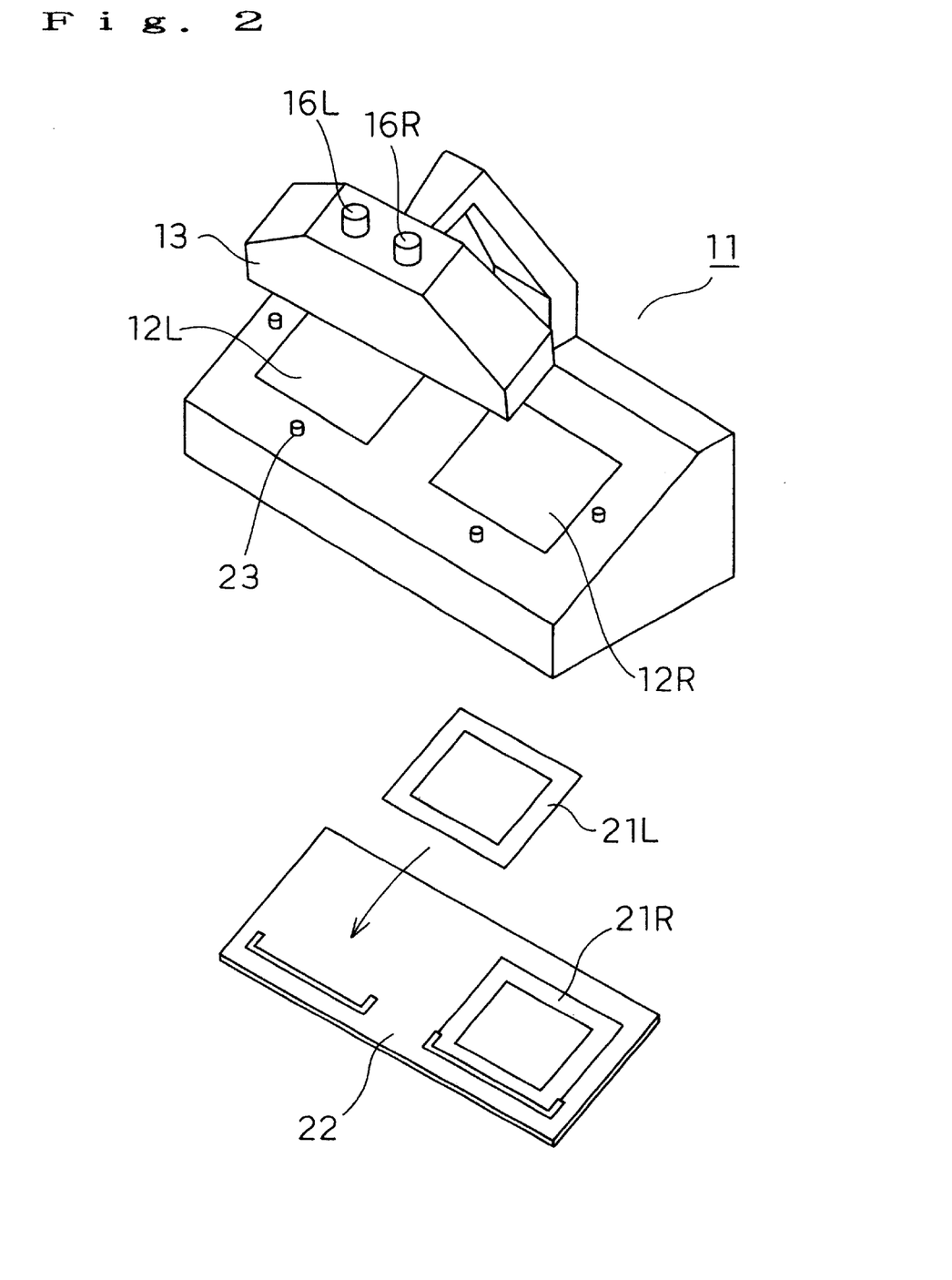
FIG. 2 is an outside view of a display unit of the embodiment 1 of the present invention.
Figure 3:
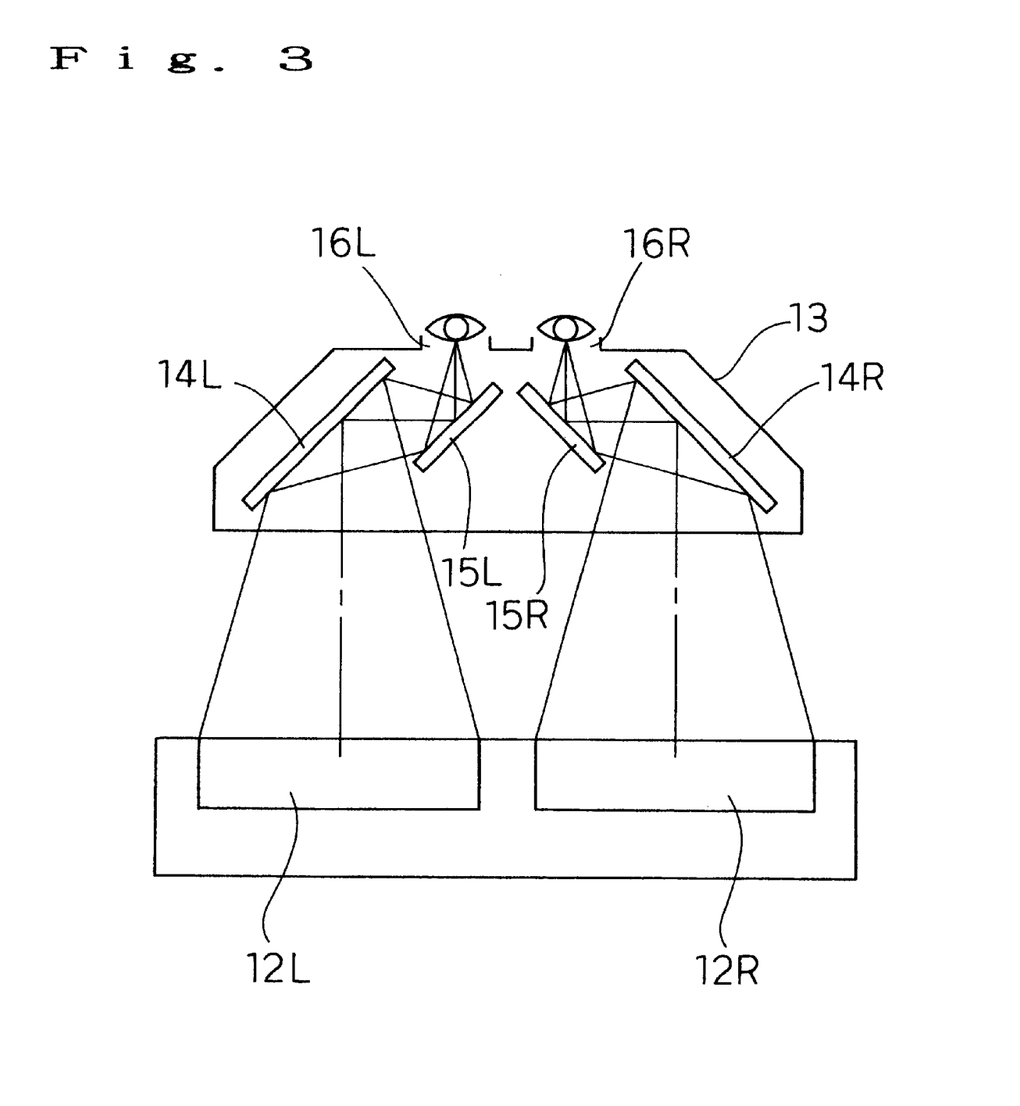
FIG. 3 is a schematic front sectional view of the display unit of the embodiment 1 of the present invention.
Figure 4:
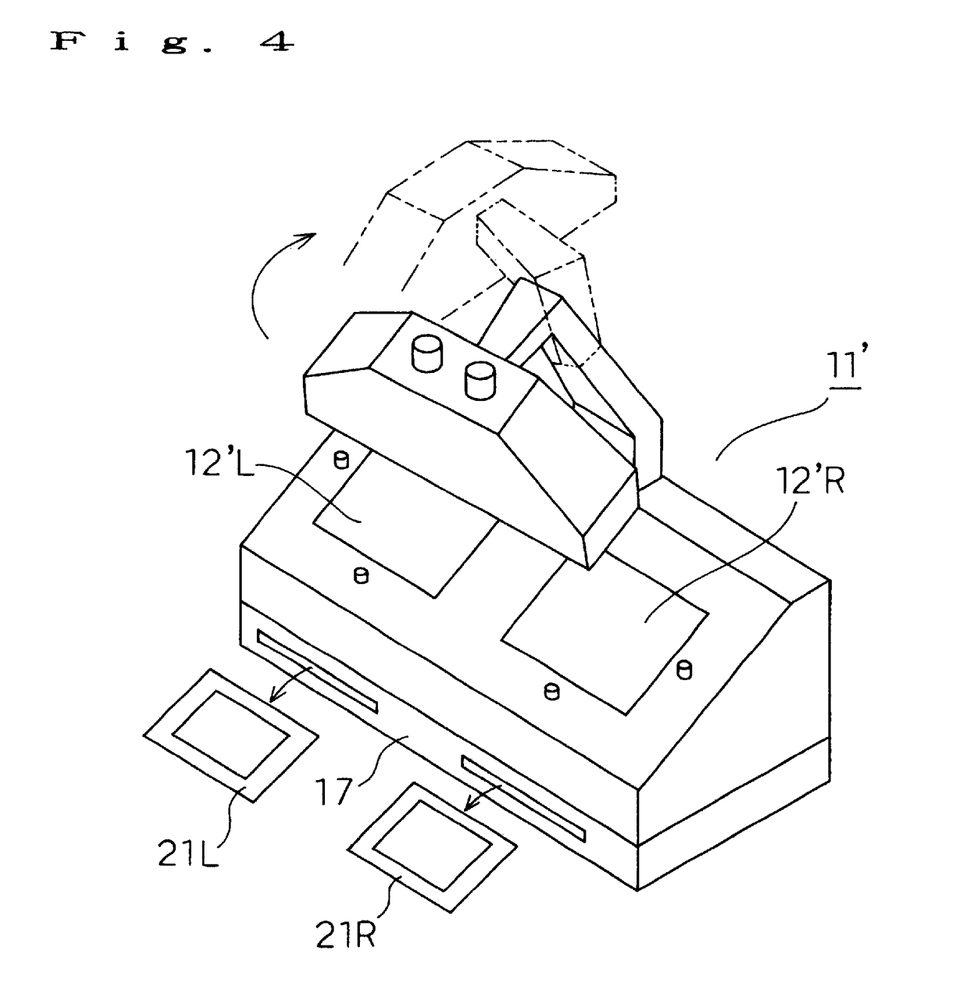
FIG. 4 is an outside view of a display unit of embodiment 2 of the present invention.
Figure 5:
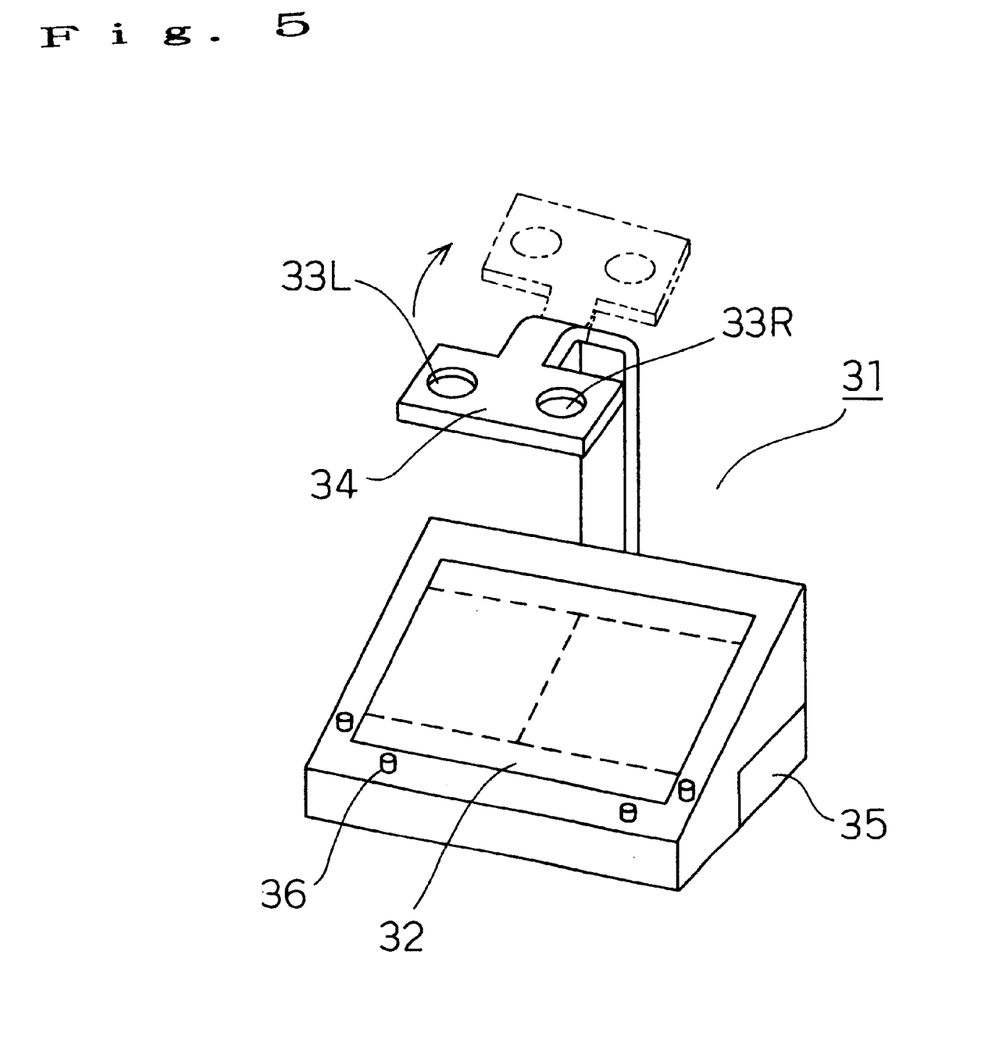
FIG. 5 is an outside view of a display unit of embodiment 3 of the present invention.

FIG. 1 is a schematic block diagram of a videoscope of the embodiment 1 of the present invention, FIG. 2 is an outside view of the display unit of the embodiment 1 of the present invention, FIG. 3 is a schematic front view of the display unit in FIG. 2, FIG. 4 is an outside view of a display unit of the embodiment 2 of the present invention, and FIG. 5 is an outside view of a display unit of the embodiment 3 of the present invention.

Symbol 1 denotes a videoscope for performing three-dimensional viewing through close-up photography, having a head portion 1a having one imaging window 2 and a grip portion 1b to be held by an observer. The head portion 1a is provided with a half mirror 3 for dividing imaging light A reflected from an object into transmitted light A1 and reflected light A2 so as to face the imaging window 2, in which an objective lens 4S and a CCD 5S serving as a first imaging system for imaging the transmitted light A1 are arranged.

Moreover, an objective lens 4K and reserve imaging device (hereafter referred to as CCD) 5K whose image-scanning direction is inverse to the normal direction serving as a second imaging system for imaging the reflected light A2 are arranged. A mirror image inverted by the half mirror 3 is output from the CCD 5K as an orthoscopic image. It is also permitted to invert a mirror image by another signal processing circuit by using a CCD having the normal scanning direction.

An optical multilayer film provided with a reflection characteristic by using a metallic film and a dielectric film is formed on the surface of the half mirror 3. Therefore, absorption is small over the entire visible range, reflectance is comparatively constant, and a polarization characteristic is small.

The objective lens 4S of the first imaging system is adjustably held by a holder 6S of the CCD 5S and the holder 6S of the CCD 5S is integrally set to an inching-mechanism portion 7S whose tilt and vertical or horizontal position can be adjusted against an optical axis.

Moreover, the objective lens 4K of the second imaging system is adjustably held by a holder 6K of the CCD 5K and the holder 6K is integrally set to an inching-mechanism portion 7K whose tilt and vertical or horizontal position can be adjusted against an optical axis.

These inching-mechanism portions 7S and 7K are one example of parallax producing means of the present invention.

A binocular parallax can be produced by the titling or horizontally shifting of the inching-mechanism portions 7S and 7K and intersectional imaging can be made by tilting and fixing the CCD 5S and 5K by an angle equal to a congestion angle. In this case, there are a method of shifting the center of an optical axis from an object and a method of adjusting the center of an optical axis to that of an object and intersectional imaging can be made by either of the methods.

Moreover, parallel imaging can be made by making optical axes of the CCDs 5S and 5K parallel and thereby, shifting, adjusting, and fixing imaging centers of them.

Furthermore, it is permitted to provide the inching-mechanism portion 7 only for one imaging system without proving the portion 7 for the other imaging system.

The inching-mechanism portion 7 can be realized by using a publicly-known art such as combination by screwing of a rotational portion for forming an angle with a slot which can be vertically and horizontally adjusted.

That is, in case of this embodiment, the imaging light A is divided into two rays through one imaging window 2 so that two rays enter the objective lenses 4S and 4K and the inching-mechanism portions 7S and 7K are used. Therefore, it is possible to realize an optimum arrangement in which the interval between centers of objective lenses forming a convergence angle is smaller than a lens diameter and set a very-small binocular parallax necessary for close-up enlargement imaging.

A camera circuit 8S of the first imaging system and a camera circuit 8K of the second imaging system are arranged on the grip portion 1b. The camera circuit 8S of the first imaging system has a synchronous driving circuit 8D to synchronously drive the camera circuit 8D of the second imaging system and the camera circuit 8S of the first imaging system by assuming the circuit 8K as a master and the circuit 8S as a slave and output synchronized first and second video signals V1 and V2.

Symbol 9 denotes a high-brightness white LED or halogen lamp for illumination, which is used to illuminate an object from the imaging window 2. Moreover, a adjusting ring 2A for adjusting a focus position is provided for the imaging window 2, which simultaneously adjusts focal distances of two imaging systems whose focal distances are adjusted from the imaging window 2.

A power supply for illumination and a power supply for a camera circuit can be integrally configured in the grip portion 1b when the power supplies are driven by a dry cell and moreover, it is permitted to use an AC power supply.

Moreover, though not illustrated, the video scope 1 is provided with static-image capturing means having two frame memories for static images and therefore, a static image can be captured by a handy switch or foot switch. In this case, it is possible to simultaneously store static images of the first and second video signals V1 and V2 or make one frame memory display a dynamic image and the other frame memory display a static image by a display selection switch.

FIG. 2 shows a display unit 11 of the embodiment 1 of the present invention, in which a first monitor screen 12R for displaying the first video signal V1 and a second monitor screen 12L for displaying the second video signal V2 are arranged at right and left on the same plane and moreover, a field-of-view limiting portion 13 for showing only the monitor screen 12R to the right eye of an observer and only the monitor screen 12L to the left eye of him is used.

As shown in FIG. 3, the display unit 11 is configured so that an observer can directly view images on the monitor screens 12R and 12L with his right and left eyes by reflecting one of the images from mirrors 14R and 15R and the other image from mirrors 14L and 15L and returning them to right and left ocular windows 16R and 16L.

That is, three-dimensional feeling is obtained by fusing two images through direct viewing referred to as the peep method. Color reproducibility is improved because no polarization filter is used and a three-dimensional display free from flicker and having a high resolution is realized because no time-sharing system is used.

Moreover, though not illustrated, to correct an individual difference between both-eye intervals, it is possible to realize a configuration for changing sight-line widths of the interval between both eyes but not greatly fluctuating an image fusing range by making the ocular windows 16R and 16L movable and interlocking a corresponding mirror angle. This configuration is an example of a sight-line-width-expanding optical system of the present invention.

Moreover, by setting a wedge prism for tilting an optical axis to the ocular windows 16R and 16L, it is possible to change sight-line widths of the interval between both eyes.

Furthermore, though not illustrated, the display unit 11 is provided with an external input terminal for inputting external right and left video signals different from the video signals V1 and V2 supplied from the videoscope 1, in Which an external unit and the videoscope 1 are selectively changed by a change-over switch and separate images can be displayed on the right and left monitors 12R and 12L, respectively.

Furthermore, the field-of-view limiting portion 13 is, for example, configured so as to be removable or rotatable in the direction of the arrow as shown in FIG. 4. When three-dimensional viewing is not performed, it is possible to directly view the monitors 12R and 12L as two independent monitors by removing the field-of-view limiting portion 13.

In this case, it is also permitted to configure a structure so that one video signal of the video scope can be input to one monitor screen and an external video signal can be input to the other monitor screen to display an affected-part image and an image of a case sample or the like or a preserved affect-part image before medical treatment and an affected-part image after medical treatment.

Moreover, it is permitted to provide the above static-image capturing means for the display unit 11.

The monitor screens 12R and 12L respectively have a size of approximately 6.5 inches which is made almost the same as the size of a print sheet of a video printer currently spread. Moreover, three-dimensional viewing is realized by mounting a print sheet 21R on which an image of the monitor screen 12R which is a right-eye image is printed out on the monitor screen 12R of the display unit 11 and a print sheet 21L on which an image of the monitor screen 12L which is a left-eye image is printed out on the monitor screen 12L of the display unit 11 and observing the images from the ocular windows 16R and 16L.

By using a cassette 22 dedicated to positioning and mounting of the print sheets 21R and 21L and by setting a stopper 23 such as a pin for positioning the cassette 23 to the display unit 11, three-dimensional viewing is more easily realized and the data for print-preserved right and left images can be three-dimensionally reproduced. The above configuration is an example of print-sheet fixing means of the present invention.

Moreover, by storing the data for right and left images in a personal computer and connecting reproduction outputs to the monitor screens 12R and 12L, three-dimensional viewing can be similarly easily reproduced and an electronic file can be obtained.

Furthermore, by using a liquid-crystal display for a monitor screen, downsizing is realized.

(Embodiment 2)

FIG. 4 shows a display unit 11' of the embodiment 2 of the present invention which is the integrated type mounting video printing means 17 for printing out images corresponding to two monitor screens 12'R and 12'L.

The display unit 11' is configured so that a simultaneous printout of right and left images or printout of only either-side image as monocular viewing can be selected. Video printing means can use a publicly-known digital-camera printer.

(Embodiment 3)

FIG. 5 shows a display unit 31 of the embodiment 3 of the present invention, which is configured by a monitor screen 32, a field-of-view limiting portion 34 having right and left ocular windows 33R and 33L, and an image synthesizing circuit 35. The image synthesizing circuit 35 is a circuit for deleting predetermined areas of images obtained from a first video-signal output V1 and a second video-signal output V2 so as to leave only central portions of the images as described below, arranging the image at right and left, synthesizing them as video signals for one frame, and outputting the video signals.

Figure 6A:
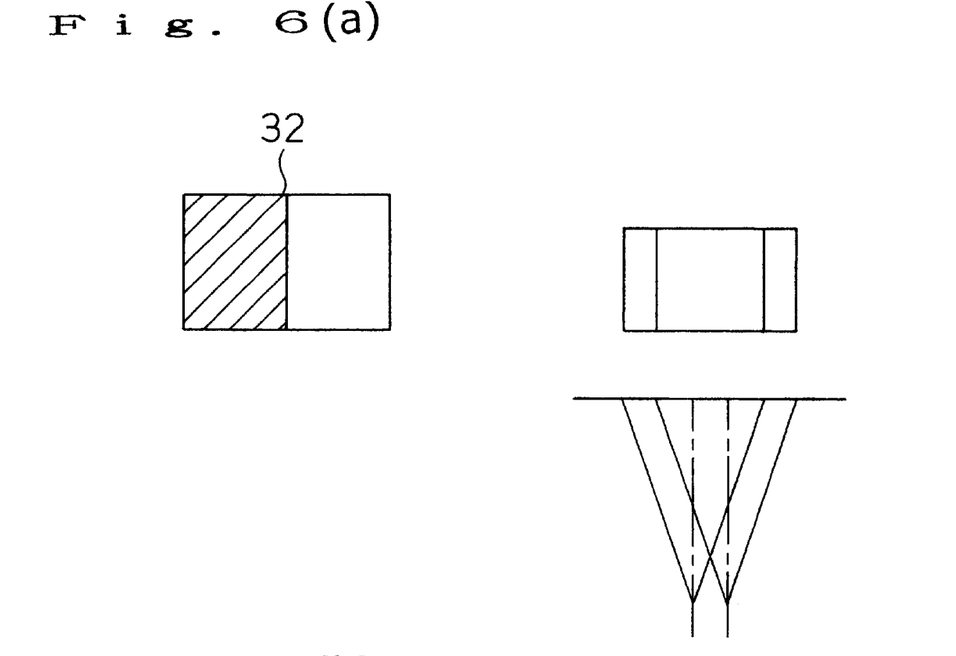
Figure 8:
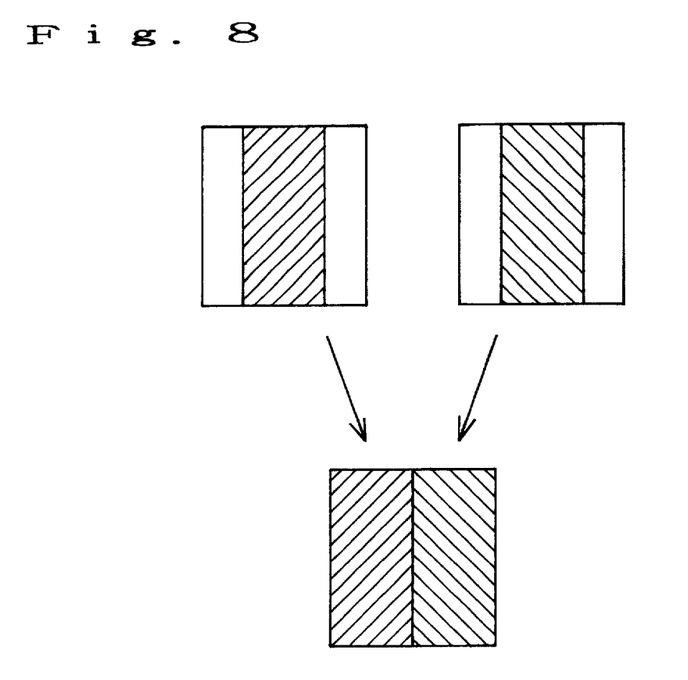
FIG. 8 is an illustration for explaining the embodiment 3 of the present invention.

That is, as shown in FIG. 8, ¼ of right and left of each image is deleted, almost ½ of the center of each image is left, and ½ images are arranged to synthesize images for one frame. This method is advantageous for the parallel imaging method because an area in which right and left images are fused is wide in the vertical direction and narrow in the horizontal direction as shown in FIG. 6(a) and thereby, an area in which images are not fused can be exclude, and preferable three-dimensional viewing is realized.

Figure 6B:
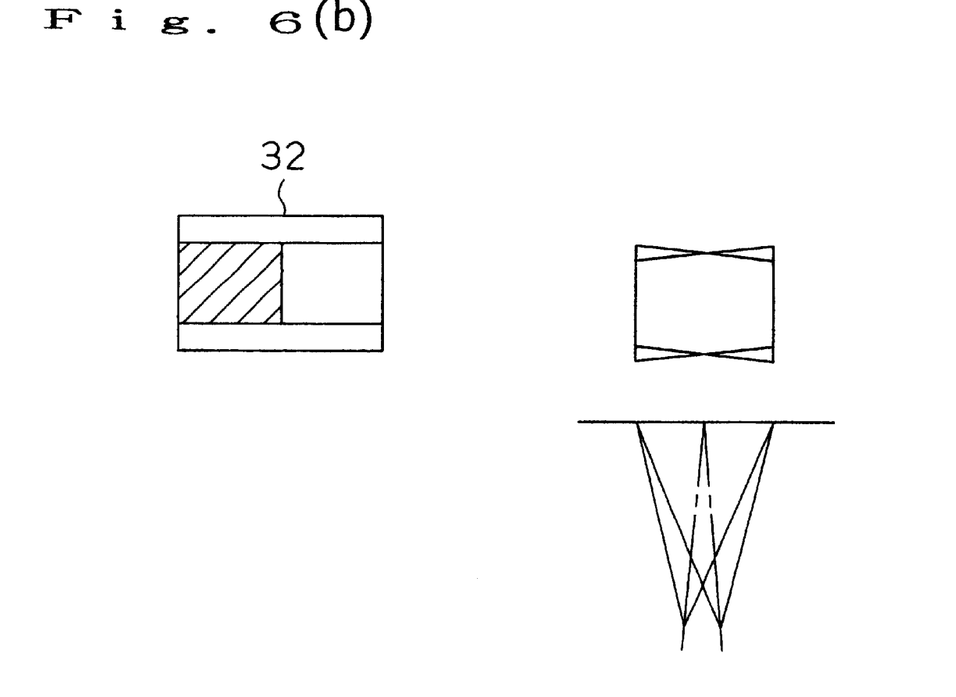
Figure 9:
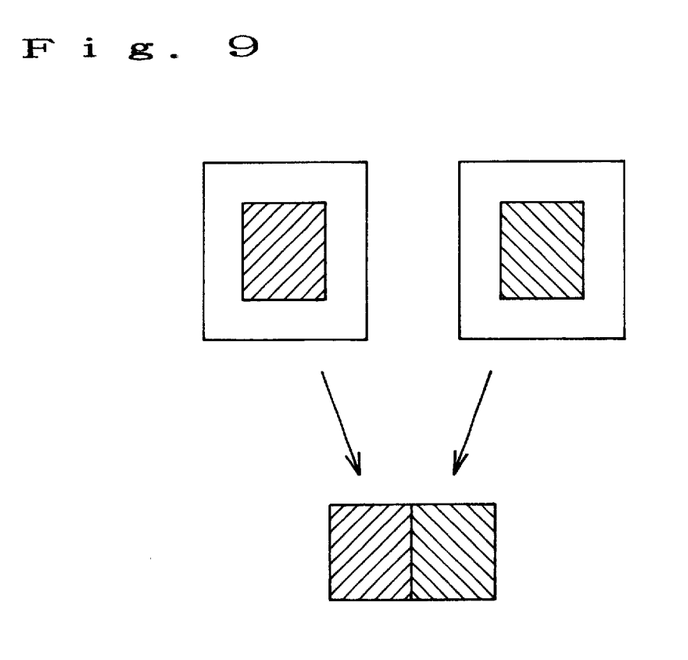
FIG. 9 is an illustration for explaining the embodiment 3 of the present invention.

In case of FIG. 9, by contrast, vertical and horizontal circumferential areas are deleted, only central portions are left, and images of only the central portions are horizontally arranged to synthesize images for one frame. This method is advantageous for the intersectional imaging method because right and left reproduced images are respectively deformed like a trapezoid and a distortion occurs even in an area in which the images are fused except the center as shown in FIG. 6(b) and therefore, the center can be taken out by excluding circumferential portions and preferable three-dimensional viewing is realized.

Moreover, it is permitted to constitute the image synthesizing circuit 35 not at the display unit-31 side but at the videoscope-1 side.

The synthesized images are displayed on one monitor screen 32 so that the right half of the monitor screen 32 can be directly viewed by the right eye of an observer and the left half of the monitor screen 32 can be directly viewed by the left eye of the observer through the right and left ocular windows 33R and 33L.

For example, the monitor screen 32 uses an approximately 7 inches-wide-type liquid-crystal monitor, in which the interval between centers of right and left images is set to 78 mm which is slightly wider than the both-eye interval of 62.5 mm (average of Japanese people) Therefore, by setting a wedge prism for tilting an optical axis to the ocular windows 33R and 33L in order to increase a sight-line width, sight-line widths of an both-eye interval are changed and thereby, it is possible to adjust right and left sight lines to centers of right and left images on the monitor screen 32.

Moreover, though not illustrated, it is permitted to make the ocular windows 33R and 33L movable in order to correct an individual difference between both-eye intervals.

Thereby, it is possible to realize a very-small configuration allowing three-dimensional viewing.

Moreover, though not illustrated, when three-dimensional viewing is not realized even by removably setting the field-of-view limiting portion 34 or rotatably setting it along an arrow direction, it is possible to configure the monitor screen 32 so that it can be directly viewed or view one image by using the monitor screen 32 as a normal monitor screen.

Furthermore, a right-and-left-arranged synthesized image is one video signal, the synthesized image can be printed out on one print sheet 36, and thereby, data can be easily preserved. By both-eye-fusion-observing the print sheet 36 alone through a stereogram or the like, it is possible to reproduce three-dimensional viewing. Moreover, by mounting and positioning the print sheet 36 on the monitor screen 32 of the display unit 31 with a stopper 36 such as a pin and observing it through the ocular windows 33R and 33L, three-dimensional viewing is realized.

In this case, however, when an image on a print sheet is small, the size of the image is adjusted by rotating a wedge prism for tiling an optical axis so that the interval between centers of right and left images becomes smaller and slight-line widths coincide with each other or the height of the field-of-view limiting portion 34 is adjusted.

Moreover, it is permitted to use a monitor having a screen size of 4:3 or display the image on a personal computer by using a videoscope mounted on an image synthesizing circuit. In this case, three-dimensional viewing is realized by using a simple field-of-view limiting means which can be mounted on the personal computer or it is simply realized even by a reproduced output of preserved data. Moreover, it is permitted to reproduce the image on the display unit 31 from the personal computer.

Furthermore, through not illustrated, it is permitted to realize an integrated configuration in which video printing means is mounted on the display unit 31. In this case, by realizing the configuration so that data can be printed out on a sheet having a size same as that of the monitor screen 32, a print image can be three-dimensionally viewed more simply without mounting the sheet on a monitor screen or changing slight-line widths.

Thus, a simple user-friendly display unit can be realized which does not require special glasses, which does not increase in size, and which can be used on a table.

As described above, the present invention makes it possible to easily obtain a very-small binocular parallax.

Moreover, the present invention makes it possible to realize a handy and easily-manipulable display unit capable of reproducing an image for three-dimensional viewing.

What is claimed is:

1. A video comprising:
light dividing means for dividing the light incoming from only one imaging window and emitted from an object, into transmitted light and reflected light;
a first imaging system having at least an objective lens and an imaging device for imaging the transmitted light; and
a second imaging system having at least an objective lens and an imaging device for imaging the reflected light, wherein:
image inverting means for returning a mirror image formed by the reflected light to an orthoscopic image is provided for the second imaging system; and
parallax producing means for producing a parallax for three-dimensionally viewing an image formed by the first and second imaging systems.

2. The videoscope according to claim 1, wherein a camera circuit of the first imaging system and a camera circuit of the second imaging system are synchronously driven by one as a master and the other as a slave to output first and second video signals synchronized to each other.

3. The videoscope according to claim 1, wherein image synthesizing means is included which produces images for one frame by deleting predetermined areas of video signals of said first and second imaging systems so as to leave central portions and arranging video signals of central portions at right and left and outputting images for one frame as video signals.

4. The videoscope according to claim 3, further comprising image-capturing means for capturing a video-signal output supplied from the image synthesizing means into a frame memory.

5. The videoscope according to claim 1, wherein:
said first and second imaging systems respectively making it possible to adjust a position of the objective lens; and
adjusting means for simultaneously adjusting focal distances of the two imaging systems is provided for the imaging window.

6. A videoscope, comprising:
light dividing means for dividing the light incoming from an imaging window and emitted from an object, into transmitted light and reflected light;
a first imaging system having at least an objective lens and an imaging device for imaging the transmitted light; and
a second imaging system having at least an objective lens and an imaging device for imaging the reflected light;
wherein image inverting means for returning a mirror image formed by the reflected light to an orthoscopic image is provided for the second imaging system;
parallax producing means for producing a parallax for three-dimensionally viewing an image formed by the first and second imaging systems; and
the image inverting means includes a mirror plane of a half mirror and is formed into an optical multilayer provided with a reflection characteristic by using a metallic film and a dielectric film.

7. A videoscope, comprising:
light dividing means for dividing the light incoming from an imaging window and emitted from an object, into transmitted light and reflected light;
a first imaging system having at least an objective lens and an imaging device for imaging the transmitted light; and
a second imaging system having at least an objective lens and an imaging device for imaging the reflected light;
wherein image inverting means for returning a mirror image formed by the reflected light to an orthoscopic image is provided for the second imaging system;
parallax producing means for producing a parallax for three-dimensionally viewing an image formed by the first and second imaging systems; and
the image inverting means uses an inverse imaging device whose image-scanning direction is inverse to the normal direction.

8. A videoscope, comprising:
light dividing means for dividing the light incoming from an imaging window and emitted from an object, into transmitted light and reflected light;
a first imaging system having at least an objective lens and an imaging device for imaging the transmitted light; and
a second imaging system having at least an objective lens and an imaging device for imaging the reflected light;
wherein image inverting means for returning a mirror image formed by the reflected light to an orthoscopic image is provided for the second imaging system;
parallax producing means for producing a parallax for three-dimensionally viewing an image formed by the first and second imaging systems; and
image-capturing means for simultaneously capturing video-signal outputs into a frame memory, generated by the first and second imaging systems.

9. A display unit, comprising image synthesizing means for producing images for one frame by deleting predetermined areas of a first video signal and a second video signal which are provided with a parallax for three-dimensional viewing so as to leave central portions and arranging video signals of central portions to right and left and outputting the images for one frame as video signals; and
image-capturing means for capturing a video-signal output supplied from the image synthesizing means into a frame memory.

* * * * *

UNITED STATES PATENT AND TRADEMARK OFFICE
CERTIFICATE OF CORRECTION

PATENT NO. : 6,674,462 B1
DATED : January 6, 2004
INVENTOR(S) : Kiyoko Ooshima et al.

It is certified that error appears in the above-identified patent and that said Letters Patent is hereby corrected as shown below:

Title page,
Item [56], References Cited, U.S. PATENT DOCUMENTS, insert -- U.S. 5,879,064 3/1999 Inaba --.
FOREIGN PATENT DOCUMENTS, delete " 2/1926" and substitute therefor
-- 2/1996 --

Signed and Sealed this

Twenty-second Day of June, 2004

JON W. DUDAS
*Acting Director of the United States Patent and Trademark Office*